United States Patent
Wright

(10) Patent No.: US 11,065,206 B2
(45) Date of Patent: Jul. 20, 2021

(54) TOPICAL FORMULATIONS INCLUDING LIPID MICROCAPSULE DELIVERY VEHICLES AND THEIR USES

(75) Inventor: David Craig Wright, Pacific Grove, CA (US)

(73) Assignee: Avidas Pharmaceuticals, LLC, Doylestown, PA (US)

( * ) Notice: Subject to any disclaimer, the term of this patent is extended or adjusted under 35 U.S.C. 154(b) by 0 days.

(21) Appl. No.: 14/129,747

(22) PCT Filed: Jun. 29, 2012

(86) PCT No.: PCT/US2012/045095
§ 371 (c)(1),
(2), (4) Date: Jul. 24, 2014

(87) PCT Pub. No.: WO2013/003803
PCT Pub. Date: Jan. 3, 2013

(65) Prior Publication Data
US 2014/0348910 A1    Nov. 27, 2014

Related U.S. Application Data

(60) Provisional application No. 61/502,810, filed on Jun. 29, 2011.

(51) Int. Cl.
| | |
|---|---|
| *A61K 9/48* | (2006.01) |
| *A61K 31/355* | (2006.01) |
| *A61K 45/06* | (2006.01) |
| *A61K 9/50* | (2006.01) |
| *A61K 9/00* | (2006.01) |
| *A61K 47/14* | (2017.01) |
| *A61K 9/06* | (2006.01) |
| *A61K 31/592* | (2006.01) |
| *A61K 31/593* | (2006.01) |

(52) U.S. Cl.
CPC .......... *A61K 9/4816* (2013.01); *A61K 9/0014* (2013.01); *A61K 9/06* (2013.01); *A61K 9/5015* (2013.01); *A61K 31/355* (2013.01); *A61K 31/592* (2013.01); *A61K 31/593* (2013.01); *A61K 45/06* (2013.01); *A61K 47/14* (2013.01)

(58) Field of Classification Search
CPC .... A61K 9/127; A61K 31/355; A61K 31/592; A61K 31/593
See application file for complete search history.

(56) References Cited

U.S. PATENT DOCUMENTS

| | | | |
|---|---|---|---|
| 4,182,330 A | 1/1980 | Michaels | |
| 4,235,871 A | 11/1980 | Papahadjopoulos | |
| 4,356,167 A | 10/1982 | Kelly | |
| 4,572,915 A * | 2/1986 | Crooks | A61K 9/1075 424/731 |
| 4,610,868 A * | 9/1986 | Fountain | A61K 9/127 264/4.1 |
| 4,725,442 A | 2/1988 | Haynes | |
| 4,744,989 A | 5/1988 | Payne | |
| 4,824,675 A | 4/1989 | Wong | |
| 4,911,928 A | 3/1990 | Wallach | |
| 5,049,391 A * | 9/1991 | Suzuki | A61K 9/1277 264/4.3 |
| 5,120,710 A | 6/1992 | Liedtke | |
| 5,152,923 A | 10/1992 | Weder | |
| 5,629,021 A | 5/1997 | Wright | |
| 5,720,948 A * | 2/1998 | Brucks | A61K 9/0014 424/78.02 |
| 5,834,016 A * | 11/1998 | Naeff | A61K 8/14 424/450 |
| 5,925,364 A * | 7/1999 | Ribier | A61K 8/0295 424/401 |
| 7,175,850 B2 * | 2/2007 | Cevc | 424/401 |
| 8,709,387 B2 * | 4/2014 | Gardner | A61K 8/67 424/60 |
| 8,784,787 B2 * | 7/2014 | Tamura | A61K 8/894 424/70.19 |
| 2004/0170582 A1 * | 9/2004 | Harivel | A61K 8/0241 424/59 |
| 2005/0175541 A1 * | 8/2005 | Lanza | A61K 9/0009 424/9.5 |
| 2008/0033027 A1 * | 2/2008 | Bascomb | A61K 31/138 514/411 |
| 2010/0080768 A1 * | 4/2010 | McGraw | A61K 9/0014 424/78.37 |

* cited by examiner

Primary Examiner — Gina C Justice
(74) Attorney, Agent, or Firm — Lange IP Law

(57) ABSTRACT

The present invention relates to topical formulations that include lipid microcapsules formed from tocopherol, tocotrienol, or mixtures thereof; a stabilizer/surfactant component; and an aqueous component. The lipid microcapsules may be formed without the use of steroids, preservatives, initiators and/or oils. The topical formulations are capable of delivering transdermal active agent(s) such as vitamin D through the skin and into the bloodstream without the use of skin penetration enhancers. In certain embodiments, the topical formulations also able to deliver topical active agent (s) such as sun-protecting agents to the surface of the skin where they remain, while simultaneously delivering the transdermal active agent(s) through the skin and into the bloodstream.

26 Claims, 3 Drawing Sheets

TOPICAL FORMULATIONS INCLUDING LIPID MICROCAPSULE DELIVERY VEHICLES AND THEIR USES

RELATED APPLICATION DATA

The present International PCT Patent Application claims priority to U.S. Provisional Patent Application No. 61/502,810, filed Jun. 29, 2011, the disclosure of which is hereby incorporated by reference in its entirety.

FIELD OF THE INVENTION

The present invention relates to topical formulations that include lipid microcapsules, in particular lipid microcapsules for the transdermal delivery of therapeutic agents into the bloodstream.

BACKGROUND OF RELATED TECHNOLOGY

Conventional delivery systems, such as for pharmaceutical agents, include lipid vesicles, which require steroids, oils and charge-producing agents (e.g., oleic acid, dactyl phosphate, cetyl sulphate, phosphatidic acid, phosphatidyl serine, and/or mixtures thereof) for their formation (see, for example, U.S. Pat. No. 4,911,928 to Wallach); and micellar nanoparticles, which contain oils and require initiators (see, for example, U.S. Pat. No. 5,629,021 to Wright).

As is known to those in the art, such conventional delivery systems have various drawbacks as a result of the ingredients used in their formation. Accordingly, there is a need in the art for new and improved delivery systems, particularly for the delivery of pharmaceutical agents. It is therefore objects of the present invention to provide such delivery systems, as well as methods for making and using the same.

SUMMARY OF THE INVENTION

In certain exemplary, non-limiting embodiments, the present inventive is directed to topical formulations which include a lipid microcapsule, the lipid microcapsule comprised of tocopherol, tocotrienol, or mixtures thereof; a stabilizer/surfactant component; and an aqueous component.

In certain exemplary, non-limiting embodiments, the tocopherol, tocotrienol, or mixtures thereof; the stabilizer/surfactant component; and the aqueous component form, in combination, a lipophilic phase of the topical formulation.

In certain exemplary, non-limiting embodiments, the tocopherol, tocotrienol, or mixtures thereof are present in the lipid microcapsule in an amount of about 0< to about 5% based on the total weight of the topical formulation.

In certain exemplary, non-limiting embodiments, the aqueous component is present in the lipid microcapsule in an amount of about 58% to about 95% based on the total weight of the topical formulation.

In certain exemplary, non-limiting embodiments, the stabilizer/surfactant component is present in the lipid microcapsule in an amount of about 7% to about 13% based on the total weight of the topical formulation.

In certain exemplary, non-limiting embodiments, the stabilizer/surfactant component of the lipid microcapsule is polyoxyethylene (2) stearyl ether or polyoxyethylene (2) cetyl ether or a mixture thereof.

In certain exemplary, non-limiting embodiments, the aqueous component of the lipid microcapsule is a physiologically compatible solution.

In certain exemplary, non-limiting embodiments, the aqueous component of the lipid microcapsule is water.

In certain exemplary, non-limiting embodiments, the topical formulation is substantially free of a skin penetration enhancer.

In certain exemplary, non-limiting embodiments, the topical formulation is substantially free of a steroid compound.

In certain exemplary, non-limiting embodiments, the topical formulation is substantially free of a preservative compound.

In certain exemplary, non-limiting embodiments, the topical formulation is substantially free of an initiator compound.

In certain exemplary, non-limiting embodiments, the topical formulation is substantially free of a charge-producing compound.

In certain exemplary, non-limiting embodiments, the topical formulation is substantially free of an oil compound.

In certain exemplary, non-limiting embodiments, the topical formulation further includes one or more transdermal active agents dissolved, suspended or encapsulated in the lipid microcapsule.

In certain exemplary, non-limiting embodiments, the one or more transdermal active agents is dissolved, suspended and/or dispersed in the aqueous component of the lipid microcapsule.

In certain exemplary, non-limiting embodiments, the one or more transdermal active agents is a vitamin D compound.

In certain exemplary, non-limiting embodiments, the vitamin D compound is present in the topical formulation in an amount of about 0< to about 30%.

In certain exemplary, non-limiting embodiments, the vitamin D compound is a physiologic biological vitamin D compound.

In certain exemplary, non-limiting embodiments, the vitamin D compound is selected from the group consisting of cholecalciferol, ergocalciferol, and mixtures thereof.

In certain exemplary, non-limiting embodiments, upon topical application of the topical formulation to a mammal, the lipid microcapsule delivers the one or more transdermal active agents transdermally to the bloodstream of the mammal.

In certain exemplary, non-limiting embodiments, the topical formulation further includes one or more topical active agents.

In certain exemplary, non-limiting embodiments, the one or more topical active agents is present outside the lipid microcapsule such that the lipid microcapsule is substantially free of the one or more topical active agents.

In certain exemplary, non-limiting embodiments, the one or more topical active agents remains substantially epicutaneous and is not substantially delivered transdermally to the bloodstream of the mammal.

In certain exemplary, non-limiting embodiments, the one or more topical active agents substantially remains on the skin of the mammal.

In certain exemplary, non-limiting embodiments, the one or more topical active agents is a sun-protecting agent.

In certain exemplary, non-limiting embodiments, the sun-protecting agent is present in the topical formulation in an amount of about 0<% to about 30% based on the total weight of the topical formulation.

In certain exemplary, non-limiting embodiments, the topical formulation is in the form of a cream, gel, liquid, lotion, solution, spray, emulsion, aerosol, or a combination thereof.

In certain exemplary, non-limiting embodiments, the present invention is directed to topical formulations including: (a) a lipid microcapsule, the lipid microcapsule comprised of tocopherol, tocotrienol, or mixtures thereof a stabilizer/surfactant component; and an aqueous component; (b) one or more transdermal active agents, the one or more transdermal active agents being dissolved, suspended or encapsulated in the lipid microcapsule; and, optionally, (c) one or more topical active agents, wherein the one or more topical active agents is present outside the lipid microcapsule such that the lipid microcapsule is substantially free of the one or more topical active agents; wherein the topical formulation is substantially free of skin penetration enhancers; and wherein, upon topical application of the topical formulation to a mammal, the one or more transdermal active agents is delivered transdermally to the bloodstream of the mammal; and the one or more topical active agents remains substantially epicutaneous and is not delivered substantially transdermally to the bloodstream of the mammal.

In certain exemplary, non-limiting embodiments, the topical formulation is substantially free of initiators.

In certain exemplary, non-limiting embodiments, the present invention is directed to methods of administration, including topically administering to a mammal a topical formulation according to the present invention.

In certain exemplary, non-limiting embodiments, the method of treatment includes topically administering a therapeutically effective amount of a topical formulation according to the present invention having a transdermal active agent that is a vitamin D compound.

In certain exemplary, non-limiting embodiments, the method of treatment is effective for the treatment of a disorder or disease associated with vitamin D deficiency or vitamin D insufficiency.

In certain exemplary, non-limiting embodiments, the method of treatment is effective for the treatment of a disorder or disease selected from the group consisting of disorders and diseases associated with low calcium uptake, bone-related disorders and diseases, vascular disorders and diseases, autoimmune disorders and diseases, tuberculosis, periodontal disease, chronic pain, seasonal affective disorder, cognitive impairment, depression, type I diabetes, chronic renal disease, hypoparathyroid, Parkinson's disease, and cancer.

In certain exemplary, non-limiting embodiments, the present invention is directed to a therapeutic method of treatment, including administering to a mammal a topical formulation according to the present invention including a sun-protecting agent.

DETAILED DESCRIPTION OF THE INVENTION

Figure 1:
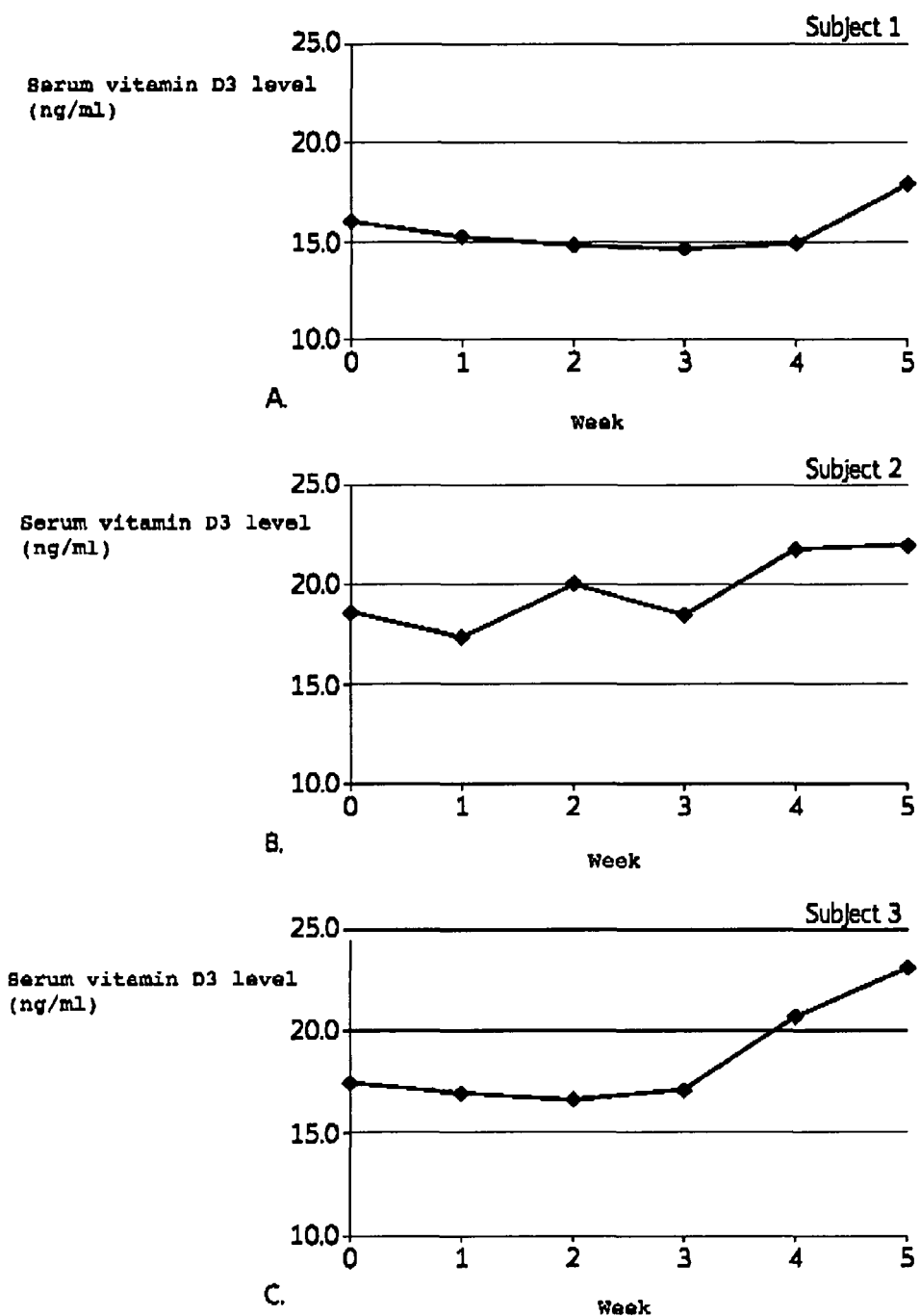
FIGS. 1A-1C show vitamin D3 levels measured from baseline (Week 0) to the end of study (Week 5). Mean increase in vitamin D3 levels was 21%.

The present invention relates to topical formulations that include lipid microcapsules, in particular lipid microcapsules for the transdermal delivery of therapeutic agents into the bloodstream.

Generally speaking, and as discussed in greater detail in the illustrative and non-limiting Examples provided herein, the present invention is directed to new topical formulations that include new lipid microcapsule delivery vehicles for the transdermal delivery of therapeutic agents into the bloodstream.

Lipid microcapsules according to the present invention include tocopherol, tocotrienol, or mixtures thereof; a stabilizer/surfactant component (such terms being used interchangeably herein), which is involved in formation of the lipid microcapsule wall; and an aqueous component, such as water or buffer.

Examples of stabilizers/surfactants which may be used in the present invention include, for example and without limitation, those set forth in Tables 1 and 2, below. It is believed that the high molecular weight of these stabilizers/surfactants imparts advantageous properties to the lipid microcapsules according to the present invention, particularly with respect to manufacture and stability.

Lipid microcapsules according to the present invention are useful as delivery system/delivery vehicles (such terms being used interchangeably herein), in particular for the therapeutic delivery of drugs and/or active agents, and more particularly for the topical delivery of hydrophilic or hydrophobic materials, for example to administer a drug and/or active agent to a patient transdermally. Lipid microcapsules according to the present invention are compatible with bodily tissues, and therefore they are useful as delivery vehicles for numerous therapeutic and other applications.

Lipid microcapsules according to the present invention are particularly useful as topical drug and active ingredient delivery vehicles as their structural characteristics permit dermal penetration. They are also exceptionally versatile in that the active agents which may be carried include those which are fat-soluble or water-soluble, and which may be suspended or dissolved. These properties allow lipid microcapsules according to the present invention to be used with ingredients that are difficult to use in conventional delivery systems, without the costs of many additive chemicals and/or enhancers.

In certain embodiments, and as described herein, lipid microcapsules according to the present invention may be formed without the use of steroids (such as cholesterol, hydrocortisone and/or analogs or derivatives thereof), preservatives, initiators (such as ethanol, methanol and other short chain alcohols and/or amides), charge-producing substances (such as oleic acid, dicetyl phosphate, cetyl sulphate, phosphatidic acid, phosphatidyl serine, and/or mixtures thereof), and/or oil ingredients, and therefore have various advantages over delivery vehicles formed using one or more such ingredients.

In certain embodiments, topical formulations according to the present invention do not require skin penetration enhancers (such as aprotic solvents, alcohols, and short chain fatty acid esters) to transdermally deliver the active agent(s) contained within the lipid microcapsules through the skin and into the bloodstream.

Additionally, lipid microcapsules according to the present invention may be modified or custom manufactured by increasing or decreasing the amount of aqueous hydration, to achieve certain desired properties.

Various other materials may optionally be added to lipid microcapsules according to the present invention, to achieve certain desired properties.

Coloring agents (such as, for example, food coloring agents), flavorings and scents may also optionally be used in forming lipid microcapsules according to the present invention, to achieve certain desired properties (for example and without limitation, in the formation of products intended for application to the lips).

Lipid microcapsules according to the present invention transport/carry (such terms being used interchangeably herein) drugs and/or active agents which are suspended and/or incorporated into the final, formed lipid microcapsules. Such drugs and/or active agent may, for example and without limitation, be dissolved, or suspended on or in the lipid microcapsules. For example and without limitation, in certain embodiments the drug and/or active agent may be cholecalciferol or ergocalciferol, which may be suspended or incorporated into lipid microcapsules according to the present invention.

The aqueous solution used to hydrate the lipophilic phase in forming lipid microcapsules according to the present invention may be, in certain embodiments, a physiologically compatible solution, such as water. The aqueous solution may have transdermal active agent(s) dissolved or suspended therein for incorporation. The basic procedure for the manufacture of lipid microcapsules according to the preset invention is to blend the tocopherol, tocotrienol and/or mixtures thereof and the stabilizer/surfactant ingredient, to thereby form a lipophilic phase. The transdermal active agent(s) to be transported, such as cholecalciferol and/or ergocalciferol, may be added and mixed in this phase. A step may be the addition to the mixture of any other ingredients, for example and without limitation, topical active agent(s) such as sun-protecting agents.

If topical active agent(s) are added to the mixture, they are not substantially suspended or encapsulated in the lipid microcapsules, and accordingly the topical formulations of the present invention may, in such an embodiment, have a bimodal functionality, wherein the single formulation is capable of delivering transdermal active agent(s) through the skin and into the bloodstream (i.e., an agent suspended or encapsulated in the lipid microcapsule) while concurrently delivering topical active agent(s) to the surface of the skin, where it remains (i.e., an agent which is not suspended or encapsulated in the lipid microcapsules).

As will be understood to those of skill in the art, the materials and processes described herein may, within the scope of the present invention, be selected and/or modified to control the properties, as desired, of the resulting lipid microcapsules according to the present invention. Active agents may, for example, be carried in the aqueous phase for suspension and incorporation into the inventive lipid microcapsules.

Furthermore, lipid microcapsules according to the present invention may be made using USP or NF grade materials suitable for human applications, such as when they are to be used for the topical delivery of a drug and/or active agent (for example, and without limitation, a fat soluble active agent such cholecalciferol or ergocalciferol) into the bloodstream.

In certain exemplary, non-limiting embodiments, lipid microcapsules according to the present invention may be used to encapsulate and deliver/transport a broad spectrum of materials; may provide a delivery vehicle for the transport of fat-soluble and/or water soluble materials; may provide a vehicle for the topical delivery of active agents such as cholecalciferol and/or ergocalciferol; may be produced in a rapid manner and/or using relatively inexpensive materials; and/or may be mixable in water and may be stored at room temperature.

According to the teachings provided herein, it is understood that those of skill in the art may produce lipid microcapsules according to the present invention incorporating drugs and/or active ingredients, and other suitable materials, including lipid microcapsules for the transdermal delivery of such drugs and/or active ingredients.

In this regard, and without limitation, lipid microcapsules according to the present invention may be formed by first combining tocopherol, tocotrienol and/or mixtures thereof and a stabilizer/surfactant ingredient (such as polyoxyethylene (2) stearyl ether (Brij 74) or polyoxyethylene (2) cetyl ether (Brij 52)).

After heating and pre-mixing of the materials, water is added to the mixture. An exemplary formulation showing the amounts of tocopherol, tocotrienol, and mixtures thereof; stabilizer/surfactant component; aqueous component, and optional sun-protecting agent that may be used is shown in Table 1; other exemplary formulations are shown in Table 2.

Unless otherwise specified, percentages provided herein refer to that based on the weight of the total formulation.

TABLE 1

Exemplary Formulation

| Ingredient | Amount |
|---|---|
| Tocopherol/Tocotrienol: Vitamin E USP | 0<% to 5% |
| Stabilizer/Surfactant (e.g., polyoxyethylene (2) stearyl ether (Brij 74) or polyoxyethylene (2) cetyl ether (Brij 52)) | 7% to 13% |
| Aqueous Solution | 58% to 95% |
| Sun-protecting agents (e.g., $ZnO_2$, $TiO_2$) | 0% to 25% (varies based on desired sun-protecting factor) |

TABLE 2

Exemplary Formulations

| | Min g* | Max g* |
|---|---|---|
| Water | 584 | 950 |
| Polyoxyethylene 2-stearyl ether | 65 | 130 |
| Alpha tocopherol | 0< | 50 |
| Cholecalciferol | 0< | 25 |
| Zinc Oxide | 24 | 253 |
| Titanium Dioxide | 0< | 102 |

*components measured in grams when admixed yield approximately 1 kg per batch

Further exemplary topical formulations of the present invention may be prepared by those of skill in the art, for example and without limitation, on the basis of the teachings provided herein, and according to the ranges of ingredients shown in Table 3.

It is to be understood that the ingredients and ranges show in Table 3 are illustrative only and are not to be viewed as a limitation on the present invention, and that each possible combination of tocopherol, tocotrienol, and mixtures thereof; stabilizer/surfactant component; aqueous component, and optional sun-protecting agent(s) shown in Table 3 is to be viewed as a separate embodiment of the present invention.

TABLE 3

Exemplary Formulations

| Ingredient | Range of Amounts |
|---|---|
| Tocopherol, Tocotrienol or Mixture | 0<% to about 20% |
| Tocopherol, Tocotrienol or Mixture | 0<% to about 15% |
| Tocopherol, Tocotrienol or Mixture | 0<% to about 10% |
| Tocopherol, Tocotrienol or Mixture | 0<% to about 5% |
| Tocopherol, Tocotrienol or Mixture | about 1% to about 5% |
| Tocopherol, Tocotrienol or Mixture | about 2% to about 5% |
| Tocopherol, Tocotrienol or Mixture | about 3% to about 5% |
| Tocopherol, Tocotrienol or Mixture | about 4% to about 5% |
| Tocopherol, Tocotrienol or Mixture | about 5% to about 9% |
| Tocopherol, Tocotrienol or Mixture | about 5% to about 8% |
| Tocopherol, Tocotrienol or Mixture | about 5% to about 7% |
| Tocopherol, Tocotrienol or Mixture | about 5% to about 6% |
| Tocopherol, Tocotrienol or Mixture | about 3% to about 4% |
| Stabilizer/Surfactant Component | about 1% to about 20% |
| Stabilizer/Surfactant Component | about 5% to about 20% |
| Stabilizer/Surfactant Component | about 5% to about 15% |
| Stabilizer/Surfactant Component | about 6% to about 14% |
| Stabilizer/Surfactant Component | about 7% to about 13% |
| Stabilizer/Surfactant Component | about 7% to about 12% |
| Stabilizer/Surfactant Component | about 7% to about 11% |
| Stabilizer/Surfactant Component | about 7% to about 10% |
| Stabilizer/Surfactant Component | about 7% to about 9% |
| Stabilizer/Surfactant Component | about 7% to about 8% |
| Stabilizer/Surfactant Component | about 10% to about 13% |
| Stabilizer/Surfactant Component | about 10% to about 12% |
| Stabilizer/Surfactant Component | about 10% to about 11% |
| Stabilizer/Surfactant Component | about 9% to about 11% |
| Aqueous Component | about 35% to about 99% |
| Aqueous Component | about 50% to about 95% |
| Aqueous Component | about 55% to about 95% |
| Aqueous Component | about 58% to about 95% |
| Aqueous Component | about 60% to about 95% |
| Aqueous Component | about 65% to about 95% |
| Aqueous Component | about 70% to about 95% |
| Aqueous Component | about 75% to about 95% |
| Aqueous Component | about 80% to about 95% |
| Aqueous Component | about 55% to about 60% |
| Aqueous Component | about 55% to about 65% |
| Aqueous Component | about 55% to about 70% |
| Aqueous Component | about 55% to about 75% |
| Aqueous Component | about 55% to about 80% |
| Aqueous Component | about 55% to about 85% |
| Aqueous Component | about 65% to about 90% |
| Cholecalciferol/Ergocalciferol | about 0.01% to about 30% |
| Cholecalciferol/Ergocalciferol | about 0.01% to about 25% |
| Cholecalciferol/Ergocalciferol | about 0.01% to about 20% |
| Cholecalciferol/Ergocalciferol | about 0.01% to about 15% |
| Cholecalciferol/Ergocalciferol | about 0.01% to about 10% |
| Cholecalciferol/Ergocalciferol | about 0.01% to about 5% |
| Cholecalciferol/Ergocalciferol | about 0.01% to about 1% |
| Cholecalciferol/Ergocalciferol | about 0.01% to about 0.5% |
| Cholecalciferol/Ergocalciferol | about 0.01% to about 0.4% |
| Cholecalciferol/Ergocalciferol | about 0.01% to about 0.3% |
| Cholecalciferol/Ergocalciferol | about 0.01% to about 0.2% |
| Cholecalciferol/Ergocalciferol | about 0.2% to about 0.3% |
| Sun-protecting Agent(s) | about 0% to about 30% |
| Sun-protecting Agent(s) | about 0% to about 25% |
| Sun-protecting Agent(s) | about 0% to about 20% |
| Sun-protecting Agent(s) | about 0% to about 15% |
| Sun-protecting Agent(s) | about 0% to about 10% |
| Sun-protecting Agent(s) | about 0% to about 5% |
| Sun-protecting Agent(s) | about 5% to about 20% |
| Sun-protecting Agent(s) | about 10% to about 20% |
| Sun-protecting Agent(s) | about 7% to about 19% |

Furthermore, capsule size may be modified by decreasing or increasing the water content; decreasing or increasing the stabilizer/surfactant content; and/or by changing the temperature or the shear in forming lipid microcapsules according to the present invention.

Other embodiments may comprise one or more combinations of the embodiments and/or examples described herein or subsets thereof.

The discussion herein and the following Examples set forth and illustrate various exemplary embodiments of the present invention, which are understood to be illustrative and non-limiting.

Example 1

Transdermal Vitamin D3 Delivery

A 5 week study was conducted to demonstrate the effectiveness of the inventive formulations to transdermally deliver vitamin D3 to increase serum vitamin D levels.

1. Materials and Methods a. Test Formulation

A vitamin D-sunscreen cream formulation of the present invention was prepared within the parameters set forth in Table 4 and as described herein ("test formulation").

TABLE 4

Test Formulation

Vitamin E USP(E)
Polyoxyethylene-1-stearyl ether (B72)
Sterile USP Water
Vitamin D3 USP (30,000 IU per gram) in corn oil
Zinc Oxide USP micronized powder (8%)

All excipients used in the test formulation were GRAS. The hydrophobic and hydrophilic components were admixed separately before combining. Zinc Oxide was admixed in the last step.

b. Subjects

Three (3) healthy subjects with screening and baseline serum vitamin D3 levels less than 30 ng/ml were selected to participate in the study. Informed consent was obtained.

Subjects agreed as follows: not to apply moisturizers or other topical skin care or prescription skin care products to the test formulation application sites during the study; to use the sunscreen on areas of potential sun exposure not covered by the test formulation; agreed to apply the test formulation once daily after bathing; to maintain their pre-study lifestyle and to not change daily activities that would change their exposure to the sun; and not to ingest vitamins or other supplements that contain any form of vitamin D within 30 days of the first visit.

c. Dosing

Subjects were dosed with the test formulation by once daily application to the neck, shoulders, arms, chest, thighs and/or abdomen following bathing, as follows: Week 1=2.5 gram; Week 2=5.0 gram; Weeks 3 and 4=10.0 gram. Application was discontinued on day 28 of the study.

d. Laboratory and Investigator Tolerability Assessments

Vitamin D3 levels were measured at Days −7 (Screening), 0 (Baseline), 7, 14, 21, 28 and 35.

Irritation, desquamation, and subject queried stinging/burning/itching at the application site of the test formulation were graded as follows: 0=None; 1=Minimal; 2=Mild; 3=Moderate; 4=Severe.

Weekly vitamin D levels between baseline and end of study were used for safety assessment (vitamin D3 excess, not to exceed 100 ng/ml at any time during the study) and local tolerability (skin irritation or other cutaneous side effects) assessments at the test formulation application sites were conducted at Days −14 to −2, 0, 7, 14, 21, 28 and 35.

e. Statistical Methods

A pre-specified endpoint was a numerically significant difference between baseline vitamin D3 and end of study vitamin D3. Vitamin D3 levels were assessed as percent change from baseline. Ordinal investigator tolerability assessments were evaluated with a Mann Whitney two-tailed t-test for nonparametric data.

2. Results

TABLE 5

Serum vitamin D3 Levels Week −1 to Week 5

| | Vitamin D3 Levels (ng/ml) | | | | | |
|---|---|---|---|---|---|---|
| Subject | Day −7 (Screen) | Day 0 (Baseline) | Day 7 | Day 14 | Day 21 | Day 28 | Day 35 |
| 1 | 14.7 | 16.0 | 15.2 | 14.8 | 14.6 | 14.9 | 17.9 |
| 2 | 18.3 | 18.6 | 17.4 | 20.0 | 18.4 | 21.8 | 21.9 |
| 3 | 16.3 | 17.5 | 17.0 | 16.7 | 17.1 | 20.7 | 23.1 |

FIGS. 1A-1C; 2A-2C; and 3A-3C show analysis of the data in Table 5, as follows:

FIGS. 1A-1C show vitamin D3 levels measured from baseline (Week 0) to the end of study (Week 5). Mean increase in vitamin D3 levels was 21% (per protocol analysis).

FIGS. 2A-2C show vitamin D3 levels measured from the lowest D3 level to the end of study (Week 5). Mean increase in vitamin D3 levels was 30% (by intent analysis).

FIGS. 3A-3C show vitamin D3 levels measured from Week 3 to the end of study (Week 5). Mean increase in vitamin D3 levels was 26% (per best case analysis).

Figure 2:
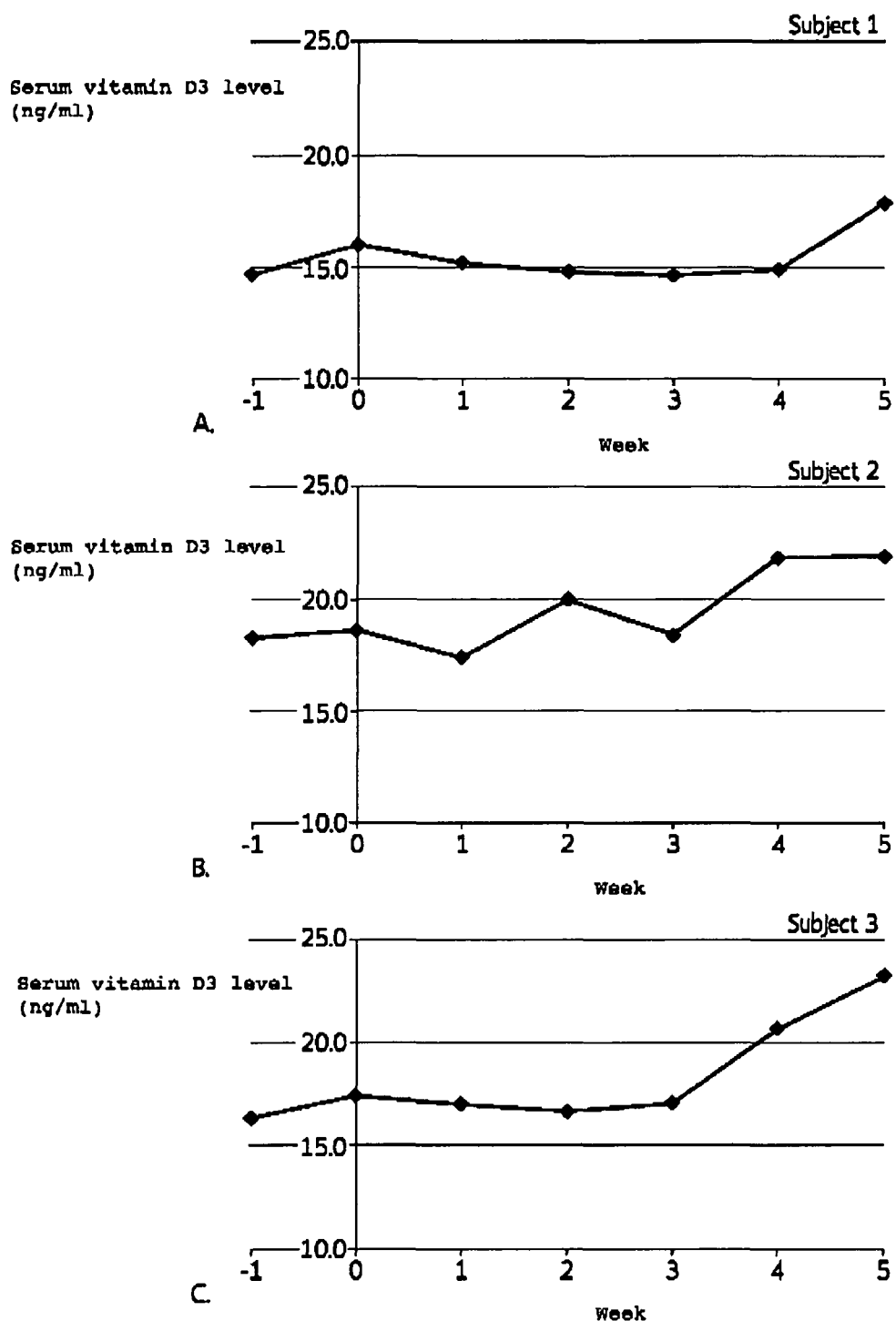
FIGS. 2A-2C show vitamin D3 levels measured from the lowest D3 level to the end of study (Week 5). Mean increase in vitamin D3 levels was 30%.
Figure 3:
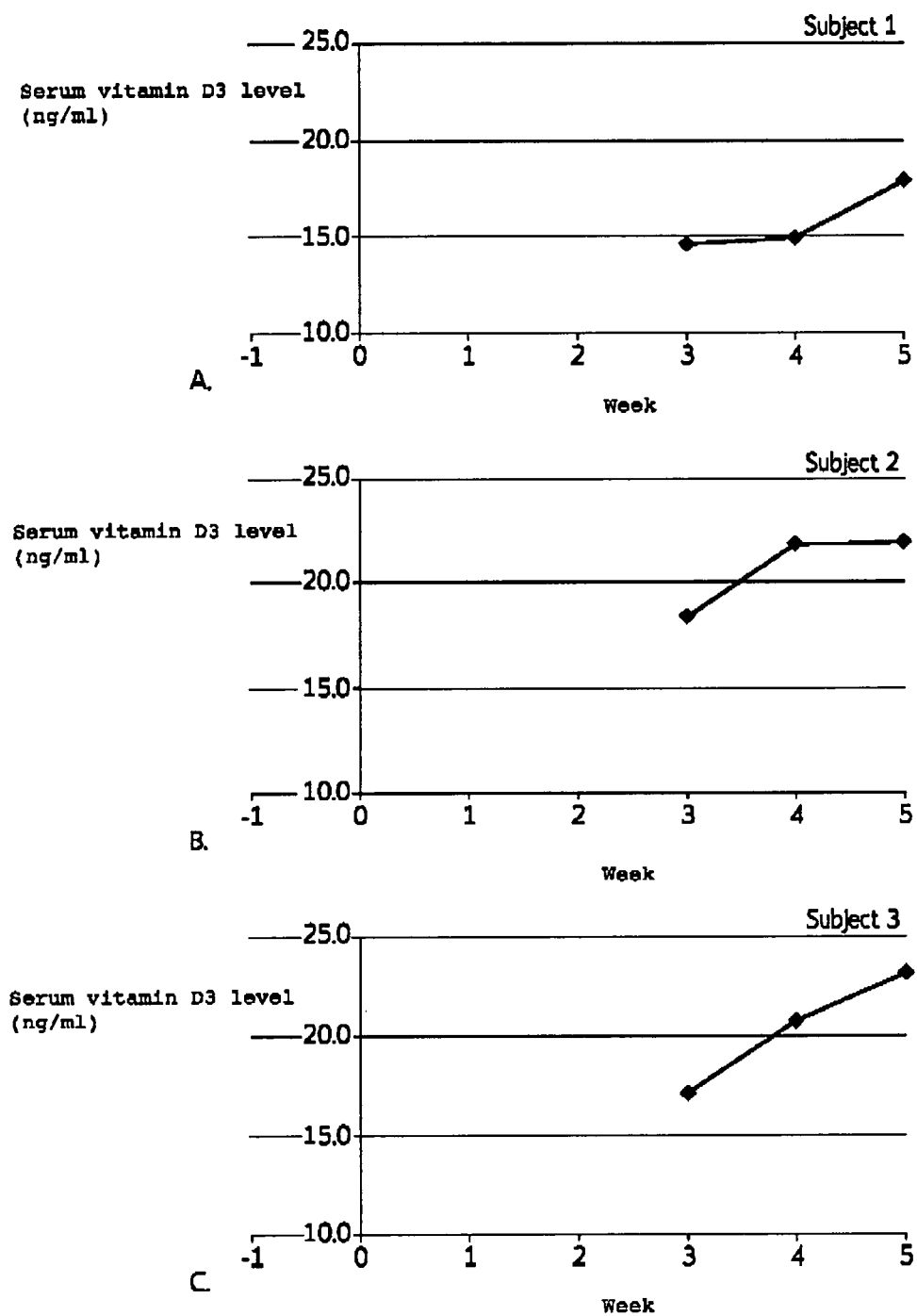
FIGS. 3A-3C show vitamin D3 levels measured from Week 3 to the end of study (Week 5). Mean increase in vitamin D3 levels was 26%.

As shown in Table 5 and as illustrated in each of FIGS. 1-3 discussed above, there was a significant increase in the serum vitamin D levels of each of Subjects 1, 2 and 3, evidencing the efficacy of the lipid microcapsules of the present invention to transdermally deliver an active agent to the bloodstream.

In certain other embodiments, and as will be understood by those of the skill in the art, topical formulations and lipid microcapsules according to the present invention may further include other ingredients, as necessary to render formulations suitable for specific applications.

Once given the above disclosure, many other features, modifications, and improvements will become apparent to the skilled artisan. Such features, modifications, and improvements are therefore considered to be part of this invention, without limitation imposed by the example embodiments described herein. Moreover, any word, term, phrase, feature, example, embodiment, or part or combination thereof, as used to describe or exemplify embodiments herein, unless unequivocally set forth as expressly uniquely defined or otherwise unequivocally set forth as limiting, is not intended to impart a narrowing scope to the invention in contravention of the ordinary meaning of the claim terms by which the scope of the patent property rights shall otherwise be determined. All references discussed and disclosed herein are hereby incorporated by reference in their entirety.

All references cited are specifically incorporated by reference in their entirety. The citation of references herein shall not be construed as an admission that such is prior art to the present invention.

REFERENCES

U.S. Pat. No. 4,182,330 to Michaels.
U.S. Pat. No. 4,235,871 to Papahadjopoulos et al.
U.S. Pat. No. 4,356,167 to Kelly.
U.S. Pat. No. 4,610,868 to Fountain et al.
U.S. Pat. No. 4,725,442 to Haynes.
U.S. Pat. No. 4,744,989 to Payne et al.
U.S. Pat. No. 4,824,675 to Wong et al.
U.S. Pat. No. 4,911,928 to Wallach.
U.S. Pat. No. 5,120,710 to Liedtke.
U.S. Pat. No. 5,152,923 to Weder et al.
U.S. Pat. No. 5,629,021 to Wright.
GB Patent No. GB2078543.
Rolland, A. et al. (1992) "New Macromolecular Carriers for Drugs. I. Preparation and Characterization of Polyoxyethylene-b-isoprene-b-oxyethylene Block Copolymer Aggregates" *Journal of Applied Polymer Science*, 44: 1195-1203.

What is claimed is:

1. A topical formulation, comprising: (a) tocopherol, tocotrienol, or mixtures thereof present in an amount of 0%< to 20% based on the total weight of said topical formulation; (b) a stabilizer/surfactant component present in an amount of 1%< to 20% based on the total weight of said topical formulation; (c) an aqueous component present in an amount of 35%< to 99% based on the total weight of said topical formulation; and (d) one or more transdermal active agents,
    wherein said tocopherol, tocotrienol, or mixtures thereof, said stabilizer/surfactant component, and said one or more transdermal active agents are mixed to produce a mixture; and said aqueous component is added to said mixture to form a lipid microcapsule within said topical formulation, wherein at least part of said aqueous component is present in said topical formulation outside of said lipid microcapsule;
    wherein said lipid microcapsule is free of a dicetyl phosphate, cetyl sulphate, phosphatidic acid or phosphatidyl serine phospholipid charge producing agent, is free of a steroid compound, is free of a fatty acid, and is free of an oil ingredient; and
    wherein said lipid microcapsule is capable of delivering one or more transdermal active agents transdermally to the bloodstream.

2. A topical formulation according to claim 1, wherein one or more of said tocopherol, tocotrienol, or mixtures thereof are present in an amount of about 0< to about 5% based on the total weight of said topical formulation.

3. A topical formulation according to claim 1, wherein said aqueous component is present in an amount of about 58% to about 95% based on the total weight of said topical formulation.

4. A topical formulation according to claim 1, wherein said stabilizer/surfactant component is present in an amount of about 7% to about 13% based on the total weight of said topical formulation.

5. A topical formulation according to claim 1, wherein said stabilizer/surfactant component is polyoxyethylene (2) stearyl ether or polyoxyethylene (2) cetyl ether or a mixture thereof.

6. A topical formulation according to claim 1, wherein said aqueous component is a physiologically compatible solution.

7. A topical formulation according to claim 1, wherein said aqueous component is water.

8. A topical formulation according to claim 1, wherein said topical formulation is free of a skin penetration enhancer.

9. A topical formulation according to claim 1, wherein said topical formulation is free of a preservative compound.

10. A topical formulation according to claim 1, wherein said topical formulation is free of an initiator compound.

11. A topical formulation according to claim 1, wherein said one or more transdermal active agents dissolved, suspended or encapsulated in said lipid microcapsule.

12. A topical formulation according to claim 11, wherein said one or more transdermal active agents is dissolved, suspended and/or dispersed in said aqueous component of said lipid microcapsule.

13. A topical formulation according to claim 11, wherein said one or more transdermal active agents is a vitamin D compound.

14. A topical formulation according to claim 13, wherein said vitamin D compound is present in said topical formulation in an amount of about 0< to about 30%.

15. A topical formulation according to claim 13, wherein said vitamin D compound is a physiologic biological vitamin D compound.

16. A topical formulation according to claim 13, wherein said vitamin D compound is selected from the group consisting of cholecalciferol, ergocalciferol, and mixtures thereof.

17. A topical formulation according to claim 11, further comprising one or more topical active agents.

18. A topical formulation according to claim 17, wherein said one or more topical active agents is present outside said lipid microcapsule such that said lipid microcapsule is free of said one or more topical active agents.

19. A topical formulation according to claim 18, wherein, upon topical application of said topical formulation to a mammal, said one or more topical active agents remains epicutaneous and is not delivered transdermally to the bloodstream of said mammal.

20. A topical formulation according to claim 19, wherein said one or more topical active agents remains on the skin of said mammal.

21. A topical formulation according to claim 17, wherein said one or more topical active agents is a sun-protecting agent.

22. A topical formulation according to claim 21, wherein said sun-protecting agent is present in said topical formulation in an amount of about 0<% to about 30% based on the total weight of said topical formulation.

23. A topical formulation according to claim 1, wherein said topical formulation is in the form of a cream, gel, liquid, lotion, solution, spray, emulsion, aerosol, or a combination thereof.

24. A method of administration, comprising topically administering to a mammal a topical formulation according to claim 1.

25. A method of treatment, comprising: topically administering a therapeutically effective amount of a topical formulation according to claim 1, wherein said transdermal active agent is a vitamin D compound.

26. A therapeutic method of treatment, comprising administering to a mammal a topical formulation according to claim 24, further comprising a sun-protecting agent.

* * * * *